United States Patent
Chaki (10) Patent No.: US 9,838,608 B2
(45) Date of Patent: Dec. 5, 2017

(54) WORK VISUAL INSPECTION DEVICE AND WORK VISUAL INSPECTION METHOD

(71) Applicant: TOKYO WELD CO., LTD., Ota-ku, Tokyo-to (JP)

(72) Inventor: Hiroaki Chaki, Ota-ku (JP)

(73) Assignee: TOKYO WELD CO., LTD., Tokyo-To (JP)

( * ) Notice: Subject to any disclaimer, the term of this patent is extended or adjusted under 35 U.S.C. 154(b) by 293 days.

(21) Appl. No.: 14/251,110

(22) Filed: Apr. 11, 2014

(65) Prior Publication Data

US 2014/0307082 A1    Oct. 16, 2014

(30) Foreign Application Priority Data

Apr. 12, 2013 (JP) ................................. 2013-084248

(51) Int. Cl.
| | | |
|---|---|---|
| *H04N 5/232* | (2006.01) | |
| *G06T 7/00* | (2017.01) | |
| *H04N 7/18* | (2006.01) | |
| *G01N 21/88* | (2006.01) | |
| *G01N 21/95* | (2006.01) | |

(Continued)

(52) U.S. Cl.
CPC ..... *H04N 5/23296* (2013.01); *G01N 21/8806* (2013.01); *G01N 21/95* (2013.01); *G02B 7/04* (2013.01); *G06T 7/0004* (2013.01); *H04N 7/18* (2013.01); *G02B 27/0075* (2013.01)

(58) Field of Classification Search
CPC ...... G01N 21/8806; G01N 21/95; G02B 7/04; G02B 27/0075; G06T 7/0004; H04N 5/23296; H04N 7/18
See application file for complete search history.

(56) References Cited

U.S. PATENT DOCUMENTS

| | | | | |
|---|---|---|---|---|
| 7,725,018 B2* | 5/2010 | Konishi | ................. | G03B 13/32 348/352 |
| 2009/0174767 A1* | 7/2009 | Kishimoto | ............. | F16J 15/108 348/92 |
| 2014/0183264 A1* | 7/2014 | Nunnink | ............ | G06K 7/10811 235/462.24 |

FOREIGN PATENT DOCUMENTS

| | | |
|---|---|---|
| CN | 102079448 A | 6/2011 |
| EP | 0 840 107 A2 | 5/1998 |
| JP | 63-085561 A | 4/1988 |

(Continued)

OTHER PUBLICATIONS

Office Action issued in corresponding Korean Patent Application No. 10-2014-0033249 dated Sep. 7, 2015 (and an English translation thereof).

(Continued)

*Primary Examiner* — Christopher S Kelley
*Assistant Examiner* — Maria Vazquez Colon
(74) *Attorney, Agent, or Firm* — Birch, Stewart, Kolasch & Birch, LLP (57) ABSTRACT

The work, visual inspection device 30 composes a conveyance table 2 which holds and conveys works W1 and W2 and camera units 8, 9, 10, 11, 12 and 13 which capture images of the works conveyed by the conveyance table, The camera 91/101 of the camera units 9 and 10 includes a first body tube 91C/101C including an imaging lens 91L/101L and a second body tube 91Ca/101a attached to the front end of the first body tube 91C/101C. The second body tube 91Ca/101Ca includes a glass plate 91G/101G for focal adjustment having two surfaces in parallel with each other.

4 Claims, 10 Drawing Sheets

(51) Int. Cl.
  *G02B 7/04*   (2006.01)
  *G02B 27/00*  (2006.01)

(56)       References Cited

FOREIGN PATENT DOCUMENTS

| | | | |
|---|---|---|---|
| JP | 03-248118 A | | 11/1991 |
| JP | 08-304043 A | | 11/1996 |
| JP | 10-062677 A | | 3/1998 |
| JP | 10062677 A | * | 3/1998 |
| JP | 2002-267913 A | | 9/2002 |
| JP | 2011-133458 A | | 7/2011 |
| JP | 5106139 B | | 10/2012 |
| WO | WO 2005/085812 A1 | | 9/2005 |

OTHER PUBLICATIONS

Office Action issued in corresponding Chinese Patent Application No. 201410140938.3 dated Aug. 2, 2016 (and English translation thereof).
Office Action issued in corresponding Japanese Patent Application No. 2013/084248 dated Sep. 30, 2016 (with English translation).

* cited by examiner

FIG. 1

| PRESENCE/ABSENCE OF GLASS | WORK TYPE | WIDTH $W_W$ [mm] OF WORK FOCUSED AT IMAGING OBJECT PLANE | DISTANCE Li [mm] FROM IMAGING OBJECT PLANE TO LENS | DIFFERENCE [mm] BETWEEN WIDTH $W_W$ OF EACH WORK AND WORK WIDTH $W_W$ CORRESPONDING TO REFERENCE FOCAL POSITION | |
|---|---|---|---|---|---|
| WITHOUT GLASS REFERENCE FOCAL POSITION $W_W$=4.5mm | No.1 | 5.5 | 109.0 | +1.0mm | WITHIN 3 mm DEPTH OF FIELD |
| | No.2 | 4.5 | 110.0 | ±0.0mm | |
| | No.3 | 4.0 | 110.5 | −0.5mm | |
| WITH GLASS REFERENCE FOCAL POSITION $W_W$=2.5mm | No.4 | 3.3 | 109.2 | +0.8mm | WITHIN 3 mm DEPTH OF FIELD |
| | No.5 | 3.2 | 109.3 | +0.7mm | |
| | No.6 | 3.0 | 109.5 | +0.5mm | |
| | No.7 | 2.5 | 110.0 | ±0.0mm | |
| | No.8 | 1.8 | 110.7 | −0.7mm | |
| | No.9 | 1.5 | 111.0 | −1.0mm | |

FIG. 2

| PRESENCE/ABSENCE OF GLASS | WORK TYPE | HEIGHT $W_H$ [mm] OF WORK FOCUSED AT IMAGING OBJECT PLANE | DISTANCE Lt [mm] FROM IMAGING OBJECT PLANE TO LENS | DIFFERENCE [mm] BETWEEN HEIGHT $W_H$ OF EACH WORK AND WORK HEIGHT $W_H$ CORRESPONDING TO REFERENCE FOCAL POSITION | |
|---|---|---|---|---|---|
| WITHOUT GLASS REFERENCE FOCAL POSITION $W_H$ = 2.5mm | No.1 | 2.7 | 109.8 | +0.2mm | ↑ WITHIN 3 mm DEPTH OF FIELD |
| | No.2 | 2.5 | 110.0 | ±0.0mm | |
| | No.3 | 1.8 | 110.7 | −0.7mm | |
| | No.4 | 1.5 | 111.0 | −1.0mm | |
| WITH GLASS REFERENCE FOCAL POSITION $W_H$ = 0.5mm | No.5 | 1.2 | 109.3 | +0.7mm | ↑ WITHIN 3 mm DEPTH OF FIELD |
| | No.6 | 1.0 | 109.5 | +0.5mm | |
| | No.7 | 0.7 | 109.8 | +0.2mm | |
| | No.8 | 0.5 | 110.0 | ±0.0mm | |
| | No.9 | 0.3 | 110.2 | −0.2mm | |

WORK VISUAL INSPECTION DEVICE AND WORK VISUAL INSPECTION METHOD

CROSS-REFERENCE TO RELATED APPLICATIONS

This patent application enjoys the benefit of Japanese Patent Application No. 2013-84248 fifed on Apr. 12, 2013, the entire disclosure of which is incorporated herein by reference.

BACKGROUND OF THE INVENTION

1. Field of the Invention

The present invention relates to a work visual inspection device and a work visual inspection method for performing the visual inspection (appearance inspection) on works (e.g., electronic components) by capturing images of surfaces of the works by using a work imaging modulo while conveying the works. In particular, the present invention relates to a work visual inspection device and a work visual inspection method with which the focal point of the work imaging module can be adjusted with ease even when the shape of the inspection object works (works as the object of inspection) is changed.

2. Description of the Related Art

There has been known a work visual inspection device that performs the visual inspection on works (e.g., electronic components each in a hexahedral shape) by setting the works on the top of a rotating disk-shaped transparent glass table, conveying the works by having them drawn to the top of the glass table by electrically charging the under surface of the glass table with a charging module (e.g., ionizer), and capturing images of surfaces of the works by using a work imaging module (see JP-A-2011-133458).

In such a work visual inspection device, the focal point of the work imaging module has to be adjusted when the shape of the work is changed (e.g., when the inspection object work is changed from a large work to a small work). However, the focal adjustment of the work imaging module requires high-accuracy adjustment work, such as precisely moving a component of the work imaging module along its optical axis.

Patent Document 1: JP-A-2011-133458

SUMMARY OF THE INVENTION

The object of the present invention, which has been made in consideration of the above-described situation, is to provide a work visual inspection device and a work visual inspection method with which the focal point of the work imaging module can be adjusted with ease even when the shape of the inspection object work is changed.

In accordance with an aspect of the present invention; there is provided a work visual inspection device comprising: a work conveyance module which holds and conveys works; and a work imaging module which captures images of the works conveyed by the work conveyance module. The work imaging module includes a first body tube including an imaging lens and a second body tube attached to the front end of the first body tube and including a transparent member for focal adjustment having two surfaces in parallel with each other.

Preferably, in the above work visual inspection device, the second body tube is attached to the first body tube by screwing the second body tube into the first body tube.

Preferably, in the above work visual inspection device, the transparent member is formed of a glass plate.

In accordance with another aspect of the present invention, there is provided a work visual inspection method comprising: a work conveyance step of holding and conveying a work with a work conveyance module; and a work imaging stop of capturing an image of the conveyed work with a work imaging module. The work imaging step includes: a first work imaging step of allowing the work imaging module to capture an image of a first work, with the work imaging module including a first body tube including an imaging lens; end a second work imaging step of allowing the work imaging module to capture an image of a second work of a shape different from the first work, with the work imaging module including the first body tube and a second body tube, the second body tube being attached to the front end of the first body tube and including a transparent member for focal adjustment having two surfaces in parallel with each other.

Preferably, in the above work visual inspection method, the second body tube is attached to the first body tube by screwing the second body tube into the first body tube.

Preferably, in the above work visual inspection method, the transparent member is formed of a glass plate.

According to the present invention, even when the shape of the inspection object work is changed, the focal point of the work imaging module can be adjusted in an easy and simple manner just by attaching/detaching the second body tube to/from the tip end of the first body tube.

DESCRIPTION OF THE PREFERRED EMBODIMENTS

Referring now to the drawings, a description will be given in detail of a preferred embodiment in accordance with the present invention.

FIGS. 1-11 are schematic diagrams showing an embodiment of a work visual inspection device in accordance with the present invention.

First, the outline of the work visual inspection device will be explained by referring to FIG. 7.

Figure 7:
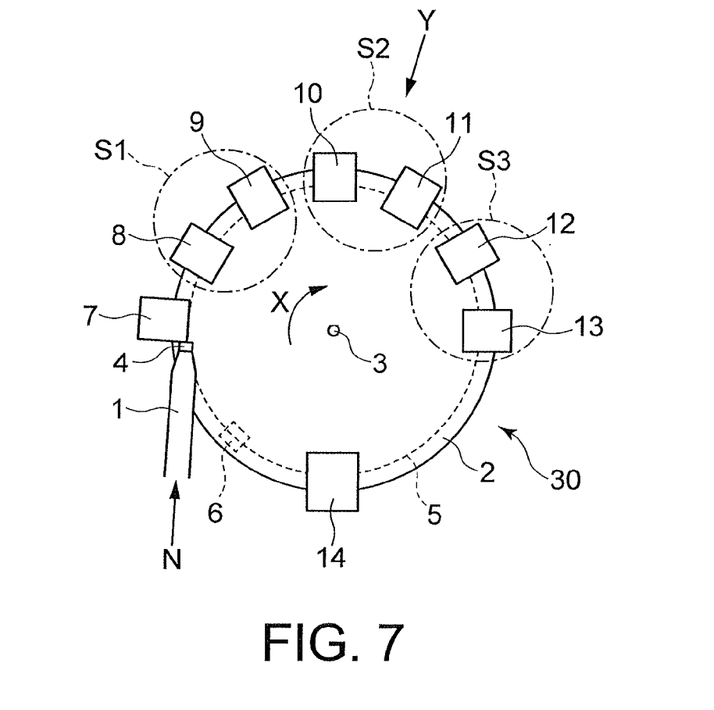
FIG. 7 is a plan view showing the work: visual inspection device in accordance with the present invention.

As shown in FIG. 7, the work visual inspection device 30 comprises a conveyance table 2 made of transparent glass for conveying a work W (e.g., electronic component in a hexahedral shape) and a side surface camera unit 8, an inner surface camera unit 9, an upper surface camera unit 10, a lower surface camera unit 11, a front surface camera unit 12 and a rear surface camera unit 13 for capturing images of the six surfaces of the work W conveyed by the conveyance table 2.

A work conveyance module is composed by the conveyance table 2, while a work imaging module is composed of the side surface camera unit 8, the inner surface camera unit 9, the upper surface camera unit 10, the lower surface camera unit 11, the front surface camera unit 12 and the rear surface camera unit 13.

In the work imaging module, the inner surface camera unit 9 is composed of a camera 91, while the upper surface camera unit 10 is composed of a camera 101. The camera 91 of the inner surface camera unit 9 includes a first body tube 91C having an imaging lens 91L and a second body tube 91Ca having a glass plate 91G as a transparent member for focal adjustment having two surfaces in parallel with each other. The camera 101 of the upper surface camera unit 10 includes a first body tube 101C having an imaging lens 101L and a second body tube 101 Ca having a glass plate 101G as a transparent member for focal, adjustment having two surfaces in parallel with each other.

Next, the camera 91 of the inner surface camera unit 9 and the camera 101 of the upper surface camera unit 10 will be explained in detail by referring to FIGS. 1-6B.

Figure 4A:
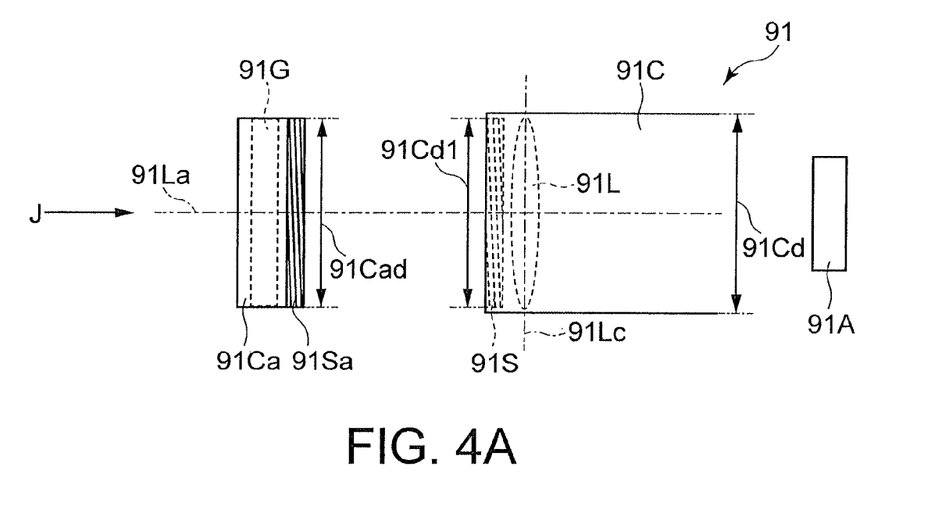
FIGS. 4A, 4B and 4C are explanatory drawings showing the inner surface camera unit of the work visual inspection device in accordance with the present invention.

The camera 91 of the inner surface camera unit 9 will be explained first by referring to FIGS. 4A-4C. FIG. 4A is a side view showing the camera 91 of the inner surface camera unit 9. The camera 91 is made up of two body tubes (first body tube 91C. second body tube 91Ca) as mentioned above.

In FIG. 4A, the first body tube 91G and the second body tube 91Ca are arranged on an optical axis 91La with their center positions aligned on the optical axis 91La. The first body tube 91C includes the imaging lens 91L. In a part inside the first body tube 91C and in the vicinity of the imaging lens 91L, a concave part having a diameter 91 Cell somewhat smaller than the diameter 91Cd of the first body tube 91C is formed, and a female thread 91S is formed on the inner surface of the concave part.

The second body tube 91Ca includes the glass pi ate 91G as the transparent member having two surfaces in parallel with each other. In a part outside the second body tube 91Ca and in the vicinity of the glass plate 91G, a male thread 91Sa having a diameter 91Cad slightly smaller than the diameter (inner diameter) of the concave part of the first body tube 91C is formed.

Figure 4B:
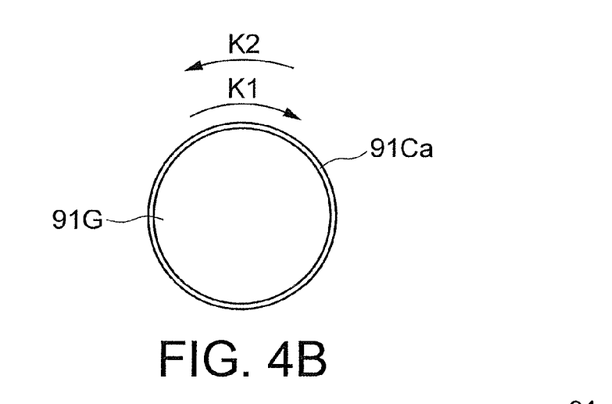

FIG. 4B is a schematic diagram showing the second body tube 91Ca viewed in the direction of the arrow J in FIG. 4A.

When the male thread 91Sa of the second body tube 91Ca shown in FIG. 4A is inserted into the concave part of the first body tube 91C and rotated in the direction of the arrow K1 in FIG. 4B, the second body tube 91Ca is attached and fixed to the first body tube 91C due to the function of the male thread 91Sa and the female thread 91S. The state of attachment is shown in FIG. 4C. The object of imaging (imaging object) is placed to the left side of the second body tube 91Ca in FIG. 4C, Thus, a state of the camera 91 without the glass plate 91G corresponds to the first body tube 91C shown in FIG. 4A, while a state with the glass plate 91G corresponds to the camera 91 (the first body tube 91C and the second body tube 91Ca) shown in FIG. 4C.

Figure 4C:
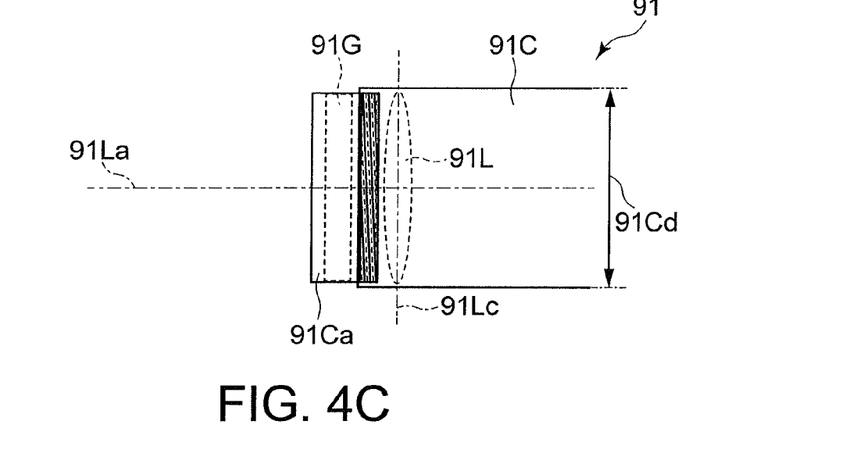

When the second body tube 91Ca in the state of FIG. 4C is rotated in the direction of the arrow K2 in FIG. 4B, the second body tube 91Ca separates from the first body tube 91C due to the function of the male thread 91Sa and the female thread 91S. As above, the second body tube 91Ca is arranged between the first body tube 91C and the imaging object (i.e., the work W shown in FIG. 8A) to be freely attachable/detachable to/from the first body tube 91C and the method of the attachment/detachment is extremely simple. Therefore, by use of this mechanism, the camera 91 can be switched between the state with the glass plate and the state without the glass plate in a simple manner and in a short time.

Figure 5A:
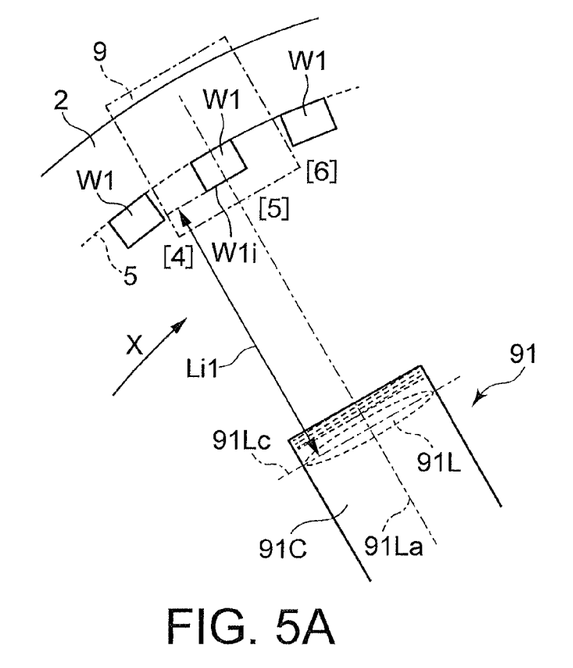
FIGS. 5A and 5B are explanatory drawings showing the operation of the inner surface camera unit of the work visual inspection device in accordance with the present invention.
Figure 5B:
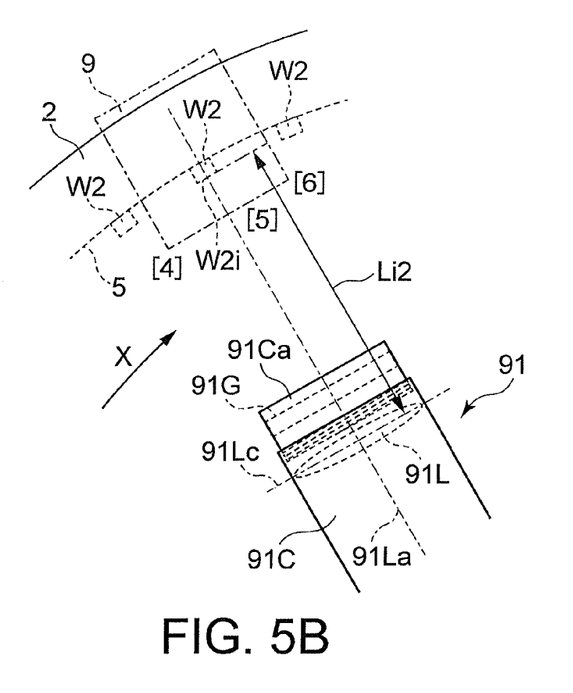

FIGS. 5A and 5B show the inner surface camera unit 9 including the camera 91 shown in FIG, 4A. FIG. 5A shows a state in which a large work W1 is shot by the camera 91, wherein the camera 91 is using the first body tube 91C only. The work W1 corresponds to works No. 1-No. 3 in FIG. 2 which will be explained later. On the other hand, FIG. 5B shows a state in which a small work W2 is shot by the camera 91, wherein the second body tube 91Ca has been attached to the first body tube 91C. The work W2 corresponds to works No. 4-No. 9 in FIG. 2 which will be explained later.

Figure 6A:
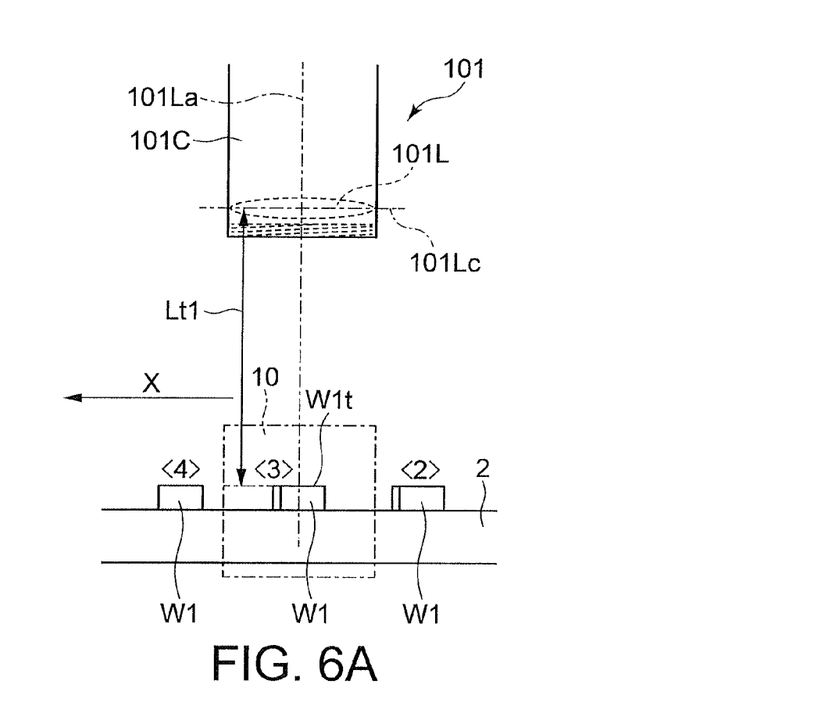
FIGS. 6A and 6B are explanatory drawings showing the operation of the upper surface camera unit of the work visual inspection device in accordance with the present invention.
Figure 6B:
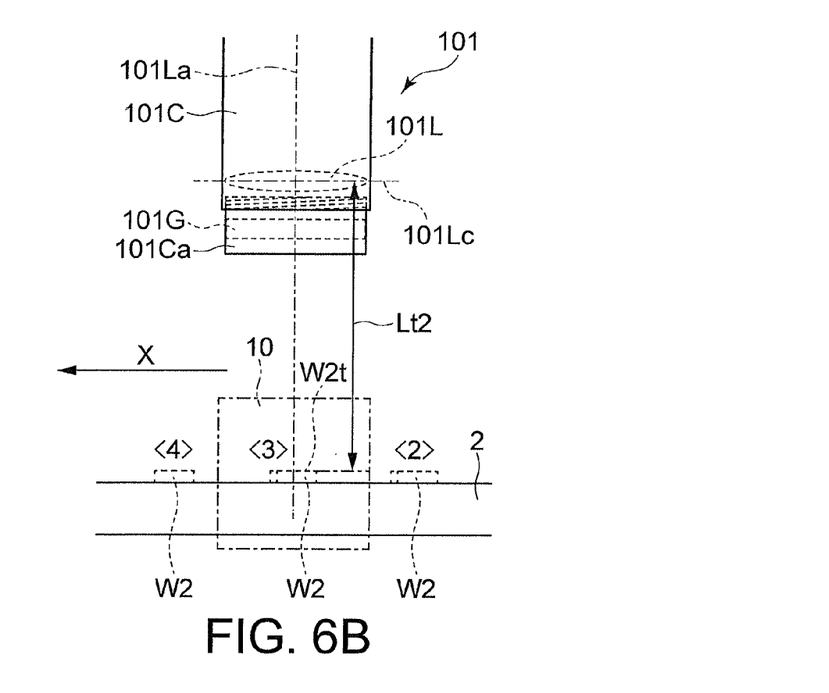

FIG. 6A and 6B show the camera 101 of the upper surface camera unit 10. FIG. 6A shows a state in which a large work W1 is shot by the camera 101, wherein the camera 101 has only the first body tube 101C storing the imaging lens 101L. The work W1 corresponds to works No. 1-No. 4 in FIG. 3 which will be explained later. On the other hand, FIG. 6B shows a state in which a small work W2 is shot by the camera 101, wherein the second body tube 101Ca storing the glass plate 101G has been attached to the first body tube 101C. The work W2 corresponds to works No. 5-No. 9 in FIG. 3 which will be explained later.

The change between the state of FIG. 5A and the state of FIG. 5B and the change between the state of FIG. 6A and the state of FIG. 5B can be made just by attaching/detaching the second body tube 91Ca or 101Ca to/from the first body tube 91C or 101C. Thus, even when the type of the inspection object works (works as the objects of inspection) is changed in the work visual inspection device 30 (see FIG. 7), the operator can handle the situation with an easy and simple operation, with no deterioration in the inspection efficiency and no physical/mental load on the operator.

Incidentally, while examples employing the glass plates 91G and 101G (as transparent members each having two surfaces in parallel with each other) are illustrated in FIGS. 4A-6B, it is also possible to employ transparent members made of a different material instead of the glass plates as long as the material is transparent.

While the mechanism for attaching the second body tube 91Ca/101Ca to the first body tube 91C/101C is made up of a male thread end female thread in the above examples, the mechanism is not restricted to this type; other types of mechanisms may also be employed for the attachment.

Next, the operation of this embodiment configured as above (i.e., the work visual inspection method) will he described below.

In the work visual inspection device 30 shown in FIG. 7, the works W are first arranged in a line and conveyed in the direction of the arrow N by a vibrating function of a linear feeder 1 which is formed in a linear shape descending at a slight tilt angle. Subsequently, at the downstream end of the linear feeder 1, each work W passes through a non-vibrated part 4 (with no vibration) and is set on the top of the transparent glass-made conveyance table 2 placed horizontally under the linear feeder X. Then, an ionizer 6 arranged directly under the conveyance table 2 and slightly before the position of the non-vibrated part 4 spouts out positive ions toward the under surface of the conveyance table 2. By the positive ions, the under surface of the conveyance table 2 is positively charged. By the effect of electrostatic induction or dielectric polarization caused by the positive charging of the under surface, the work W is drawn to the top of the conveyance table 2.

The works W adhering to the top of the conveyance table 2 are conveyed by the rotation of the conveyance table 2 (in the direction of the arrow X around the central axis 3) and are lined up on a work conveyance arc 5 (supposed to be set in the vicinity of the periphery of the top of the conveyance table 2) by the function of an alignment guide 7. Then, images of the surfaces of each of the works W being conveyed in the aligned state are captured successively by the corresponding imaging modules at the side surface camera unit 8, the inner surface camera unit 9, the upper surface camera unit 10, the lower surface camera unit 11, the front surface camera unit 12 and the rear surface camera unit 13 (visual inspection).

Each work W after undergoing the visual inspection is unloaded by an unloading unit 14 from the work conveyance arc 5 to an unshown storage box according to the result of the visual inspection.

Figure 8A:
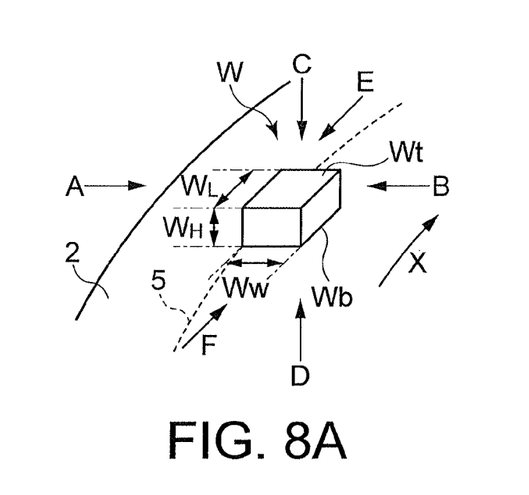
FIGS. 8A and 8B are schematic diagrams showing a state in which a work set on the top of a conveyance table is conveyed.

FIG. 8A is a perspective view showing a state in which a work W set on the top of the conveyance table 2 is conveyed. The work W is in a hexahedral shape. As shown in FIG. 8A, the length of each side of the work W in the lengthwise direction (along the rotational direction of the conveyance table 2 indicated by the arrow X) is WL The length of each side of the work W in the width direction (along the radial direction from the central axis 3 (FIG. 7) toward the periphery of the conveyance table 2) is WW. The length of each side of the work W in the height direction (pointing upward from the top of the conveyance table 2) is WITH The lengths WL, WW and WH of the sides of the work W are all within the range of approximately 1 mm-10 mm.

Figure 8B:
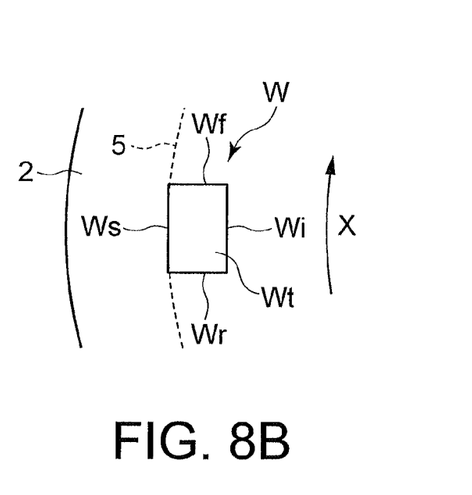

FIG. 8B is a plan view showing the work W in FIG. 8A viewed from above the conveyance table 2 (in the direction of the arrow C). In FIG. 8B, the work W has been set on the top of the conveyance table 2 so that the side surface Ws facing the outside of the conveyance table 2 is situated on the tangential line of the work conveyance arc 5. The inner surface Wi opposing the side surface Ws is facing the central axis 3 (FIG. 7) of the conveyance table 2. The front surface Wf and the rear surface Wr are facing forward and backward in the rotational direction of the conveyance table 2 indicated by the arrow X.

As shown in FIG. 8A, the length WL is in the lengthwise direction of the work W. As explained above, in the work visual inspection device 30, the work W in a hexahedral shape has been set on the top of the conveyance table 2 so that the lengthwise direction of the work W is along the rotational direction of the conveyance table 2 and the side surface Ws faces the outside of the conveyance table 2 and is situated on the tangential line of the work conveyance arc 5 by the functions of the linear feeder 1 and the alignment guide 7 shown in FIG. 7.

Here, the correspondence between each surface of the work W and each camera unit for shooting each surface will be described below. First, in the side surface camera unit 8 shown in FIG. 7, the side surface Ws shown in FIG. 8B is shot in the direction of the arrow A in FIG. 8A. Subsequently, in the inner surface camera unit 9 shown in FIG. 7, the inner surface Wi shown in FIG. 8B is shot in the direction of the arrow B in FIG. 8A. Subsequently, in the upper surface camera unit 10 shown in FIG. 7, the upper surface Wt shown in FIG. 8A is shot in the direction of the arrow C in FIG. 8A. Subsequently, in the lower surface camera unit 11 shown in FIG. 7, the lower surface Wb shown in FIG. 8A is shot in the direction of the arrow D in FIG. 8A. Subsequently, in the front surface camera unit 12 shown in FIG. 7, the front surface Wf shown in FIG. 8B is shot in the direction of the arrow E in FIG. 8A. Finally, in the rear surface camera unit 13 shown in FIG. 7, the rear surface Wr shown in FIG. 8B is shot in the direction of the arrow f in FIG. 8A.

The works W as the objects of the visual inspection by the work visual inspection device 30 can include various types of works, and thus there are cases where the type of the inspection object work is changed. In such cases, the lengths of the sides of the work (the length WL of each side in the lengthwise direction, the length WW of each side in the width direction, and the length WH of each side in the height direction shown in FIG. 8A) change due to the change in the type of the inspection object work. As a schematic diagram showing such a case where the inspection object work has been changed to a work in a different size, an enlarged view of the area S1 in FIG. 7 in the vicinity of the side surface camera unit 8 and the inner surface camera unit 9 is shown in FIG. 9.

Figure 9:
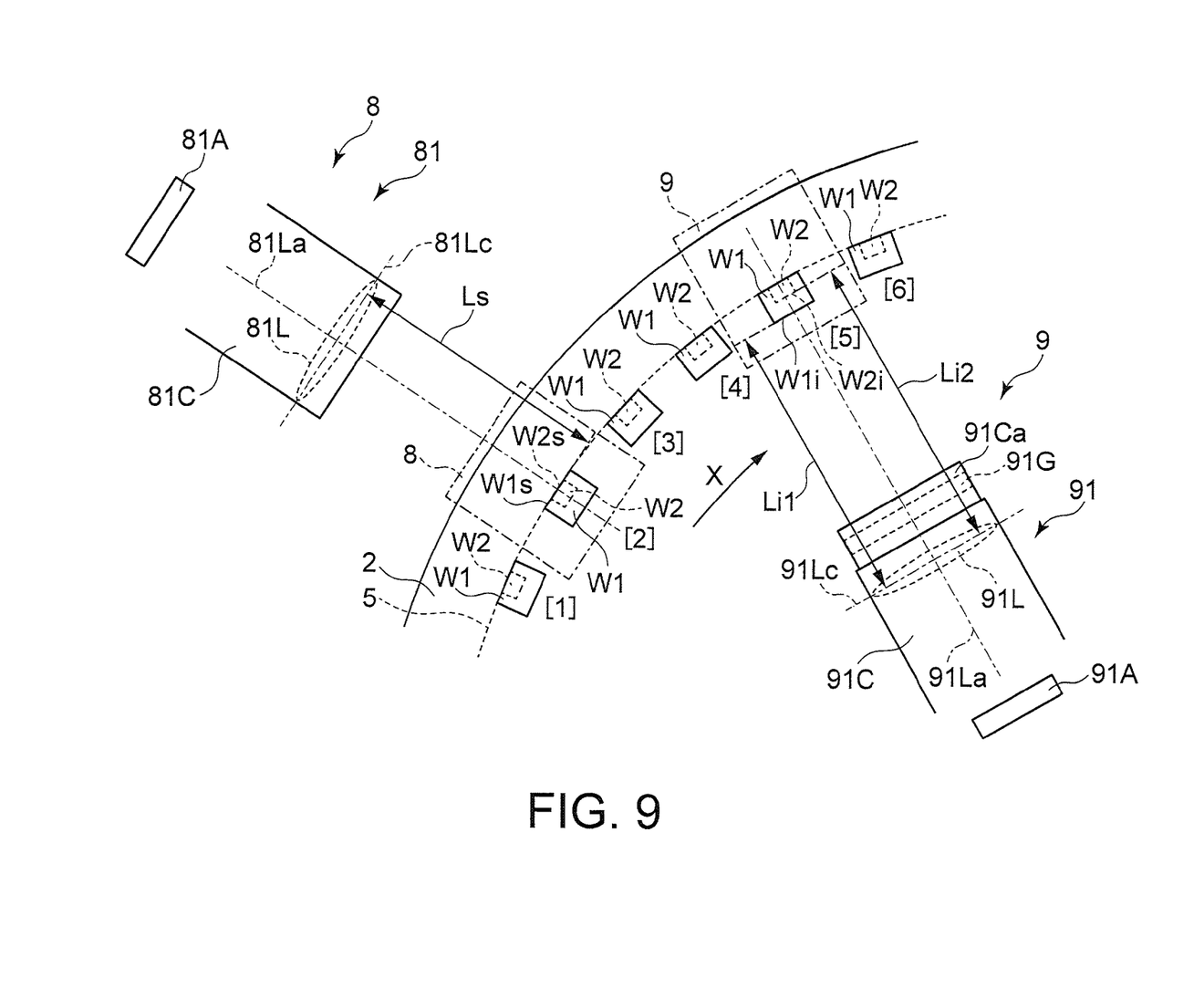
FIG. 9 is an enlarged view showing an area S1 in FIG. 7.

In FIG. 9, the work W1 before the work type change (change in the work type) is indicated by solid lines and the work W2 after the work type change is indicated by broken lines. Thus, both types of works W1 and W2 before and after the work type change are shown at the same line in FIG. 9 in regard to a case where the inspection object work has been changed from a large work W1 to a small work W2.

Along the conveyance path of the work W1/W2, positions of the work along the time line are indicated by the numbers [1]-[6]. The numbers [1]-[6] are used not to represent particular positions on the top of the conveyance table 2 but Just to indicate the conveyance of the work W1/W2 in the numerical order. As mentioned above, each work W1/W2 has been set on the top of the conveyance table 2 so that its side surface W1s/W2s faces the outside of the conveyance table 2 and is situated on the tangential line of the work conveyance arc 5. Thus, when each type of work W1/W2 has been conveyed from the position [1] to the position [2] corresponding to the side surface camera unit 8, the side surfaces W1s and W2s to be shot are situated substantially on the same plane.

In the side surface camera unit 8, a camera 81 is arranged outside the conveyance table 2. The camera 81, having a body tube SIC storing an imaging lens 81L, captures an image of the side surface W1s/W2s of the work W1/W2 with a photoreceptor device 81A when the approximate center of the side surface W1s/W2s coincides With the optical axis 81La (position [2]).

At this point, the distance Ls between the center 81Lc of the imaging lens 81L and the side surface W1s/W2s to be shot is substantially equal between the works W1 and W2. In other words, at the position [2] of the side surface camera unit 8, both the side surfaces W1s and W2s are situated at the same focal position of the imaging lens 81L. Therefore, no problem occurs in the image capturing in the side surface camera unit 8 even when the inspection object work is changed from a large work W1 to a small work W2.

Subsequently, the work W1/W2 is conveyed to the position [5] corresponding to the inner surface camera unit 9 via the positions [3] and [4] by the rotation of the conveyance table 2 in the direction of the arrow X. In the inner surface camera unit 9, the camera 91 is arranged inside the circumference of the conveyance table 2. The camera 91, having the body tube 91C storing the imaging lens 91L, captures an image of the inner surface W1i/W2i of the work W1/W2 with a photoreceptor device 91A when the approximate center of the inner surface W1i/W2i coincides with the optical axis 91La (position [5]).

In this case, the side surfaces W1s and W2s are situated substantially on the same plane as mentioned above. Further, the length WW (FIG. 8A) of each side of the work W2 in the width direction is less than that of the work W1. Thus, when the inspection object work is changed from a large work W1 to a small work W2, the distance U2 between the center 91Lc of the imaging lens 91L and the inner surface W2i of the work W2 to be shot in the inner surface camera unit 9 after the work type change becomes greater than the distance Li1 between the center 91Lc of the imaging lens 91L. and the inner surface W1i of the work W1 shot before the work type change.

At the position [5], both the inner surfaces W1i and W2i of the works W1 and W2 have to be situated at the focal position of the imaging lens 91L. Assuming here that the inner surface W1i before the work type change was exactly at the focal position of the imaging lens 91L (distance Li1), focusing on the inner surface W2i after the work type change by using the camera 91 without change is possible under the following condition where the difference between the distance Li2 (between the center 91Lc of the imaging lens 91L and the inner surface W2i to be shot after the work type change) and the distance Li1, i.e, the difference ΔLi between the length WW (FIG. 8A) of the work W1 before the work type change in the width direction and the length WW (FIG. 8A) of the work W2 after the work type change in the width direction is within the range of the depth of field of the imaging lens 91L.

Here, the "depth of field" means the focal range of an imaging lens for a camera in which image capturing in a focused state is possible even when the object is positioned slightly closer to or farther from the focal position (focused position) of the imaging lens.

In contrast, when the aforementioned difference ΔLi deviates from the range of the depth of field of the imaging lens 91L, it becomes impossible to focus on the inner surface W2i after the work type change by using the camera 91 without change, and thus there arises the need of adjusting the camera 91 after the work type change to allow the distance Li2 to be in the focused range. Specifically, the adjustment is made by the focusing of the camera 91 or by moving the position of the camera 91 on the optical axis 91La.

However, the lengths WL, WW and WH of the sides of the work W shown in FIG. 8A are all within the range of approximately 1 mm-10 mm as mentioned above and the depth of field of the imaging lens 91L is approximately 3 mm-5 mm at most. Therefore, extremely high accuracy is required in the aforementioned adjustment by the focusing of the camera 91 or by moving the position of the camera 91 on the optical axis 91La, which leads to a deterioration in the inspection efficiency (due to a long time necessary for the adjustment work) and an extremely heavy physical/mental load on the operator.

In this embodiment, the second body tube 91Ca storing the glass plate 91G is screwed into the first body tube 91C (storing the imaging lens 91L of the camera 91) in such cases. With the configuration and operation, the focusing (focal adjustment) of the camera 91 can be carried out with ease.

Figure 10:
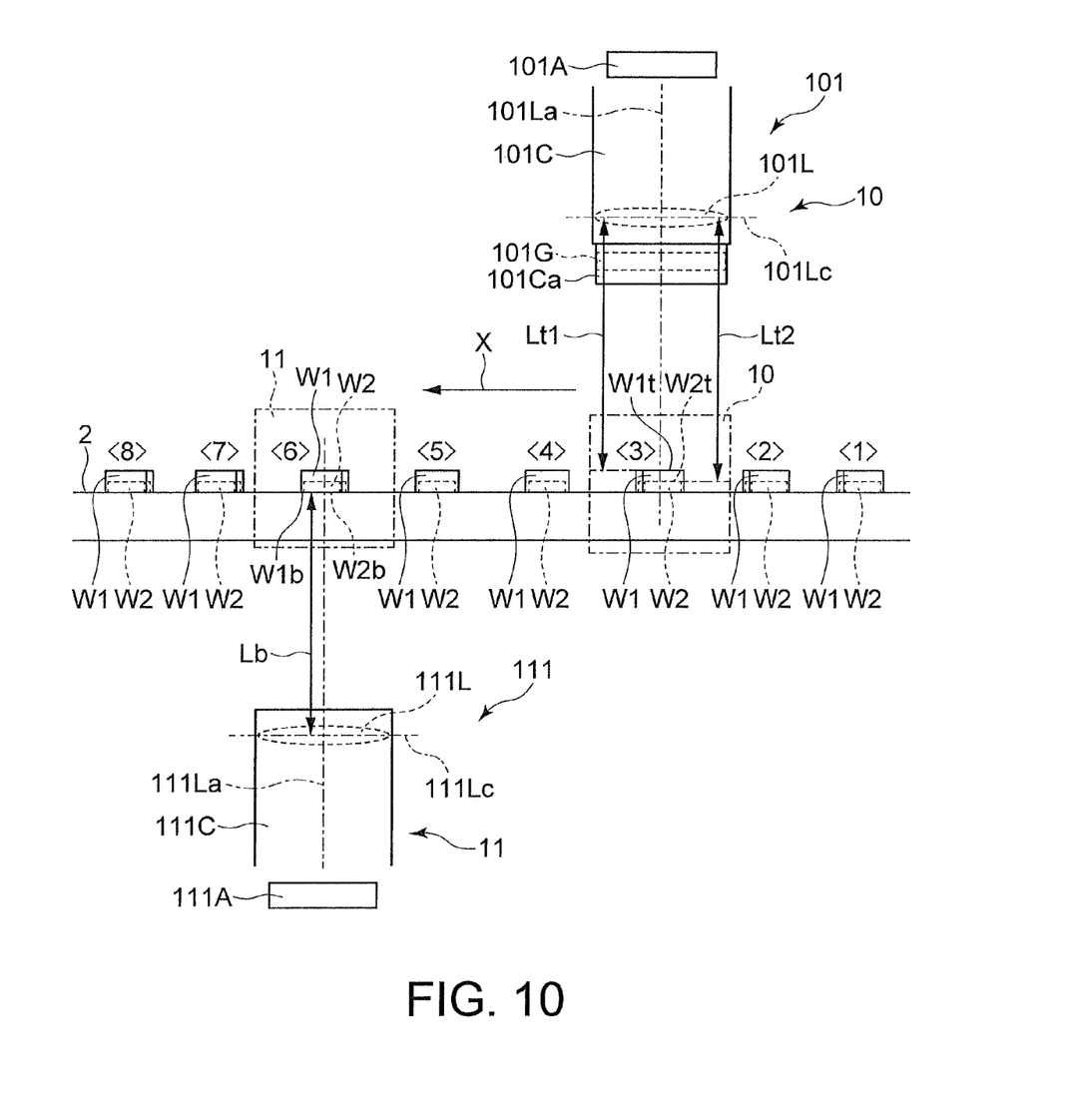
FIG. 10 is an enlarged view showing an area S2 in FIG. 7.

There also exist other positions where the focal position changes due to the change in the type of the inspection object work. FIG. 10 is an enlarged view showing the area S2 in FIG. 7 in the vicinity of the upper surface camera unit 10 and the lower surface camera unit 11 viewed in the direction of the arrow Y.

In FIG. 10, the work W1 before the work type change is indicated by solid lines and the work W2 after the work type change is indicated by broken lines in the same ways as FIG. 9, Similarly to FIG. 9, positions of the work: W1/W2 along the time line are indicated by the numbers <1>-<8> along the conveyance path of the work W1/W2.

Both the lower surfaces W1b and W2b of the works W1 and W2 are in contact with the fop of the conveyance table 2 as mentioned above, that is, the lower surfaces W1b and W2b are situated substantially on the same plane. The work W1/W2 is conveyed to the position <3> corresponding to the upper surface camera unit 10 via the positions <1> and <2> by the rotation of the conveyance table 2 in the direction of the arrow X.

In the upper surface camera unit 10, the camera 101 is arranged over the conveyance table 2. The camera 101, having the body tube 101C storing the imaging lens 101L, captures an image of the upper surface W1t/W2t of the work W1/W2 with a photoreceptor device 101A when the approximate center of the upper surface W1t/W2t coincides with the optical axis 101La (position <3>). In this case, the lower surfaces W1b and W2b are situated substantially on the same plane as mentioned above. Further, the length WH (FIG. 8A) of each side of the work W2 in the height direction is less than that of the work W1.

Thus, when the inspection object work is changed from a large work W1 to a small work W2, the distance Lt2 between the center 101Lc of the imaging lens 101L and the upper surface W2t of the work W2 to be shot in the upper surface camera unit 10 after the work type change becomes greater than the distance Lt1 between the center 101Lc of the imaging lens 101L and the upper surface With of the work W1 shot before the work type change. At the position <3>, both the upper surfaces W1t and W2t of the works W1 and W2 have to be situated at the focal position of the imaging lens 101L.

Therefore, similarly to the case of the inner surface camera unit 9 shown in FIG. 9, focusing on the upper surface W2t after the work type change by using the camera 101 without change is possible under the following condition where the difference between the distance Lt2 (between the center 101Lc of the imaging lens 101L and the upper surface W2t to be shot after the work type change) and the distance Lt1, i.e., the difference ΔLt between the length WH (FIG. 8A) of the work W1 before the work type change in the height direction and the length WH (FIG. 8A) of the work W2 after the work type change in the height direction is within the range of the depth of field of the imaging lens 101L. In contrast, when the aforementioned difference ΔLt deviates from the range of the depth of field of the imaging lens 101L, it becomes impossible to focus on the upper surface W2t after the work type change by using the camera 101 without change, and thus there arises the need of adjusting the camera 101 after the work type change to allow the distance Lt2 to be in the focused range.

In this embodiment, the second body tube 101Ca storing the glass plate 101G is screwed into the first body tube 101C (storing the imaging lens 101L of the camera 101) in such cases. With the configuration and operation, the focusing (focal adjustment), of the camera 101 can be carried out with ease.

Next, the focusing (focal adjustment) of the camera 91 of the inner surface camera unit 9 and the camera 101 of the upper surface camera unit 10 will be explained below.

Figure 1:
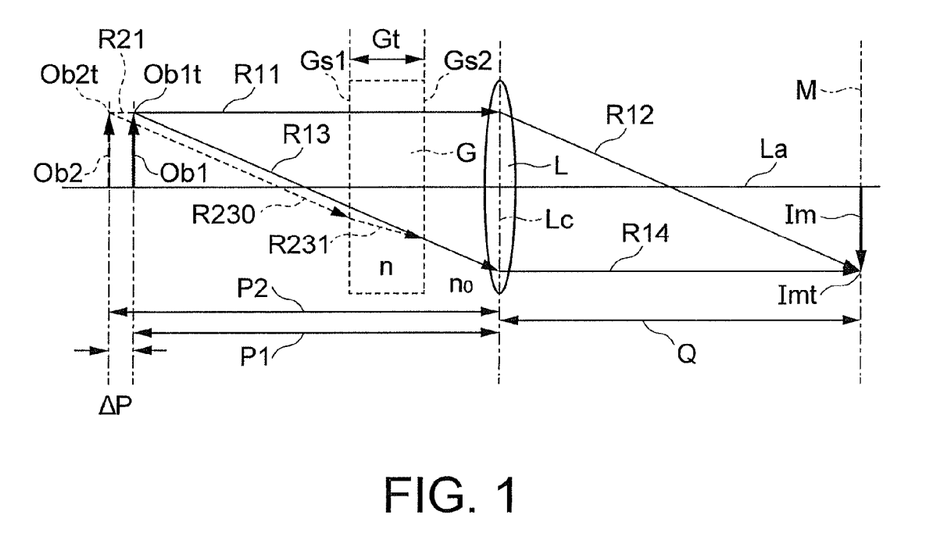
FIG. 1 is an explanatory drawing showing the basic principle of a work visual inspection device in accordance with the present invention.

The basic principle of the focusing (focal adjustment) is shown in FIG. 1. In FIG. 1, a first object Ob1 (solid line arrow) is placed at a position a distance P1 leftward from the center Lc of an imaging lens L (corresponding to the imaging lenses 91L and 101L) of a camera. Rays of light propagating from the tip end part Ob1t of the first object Ob1 to the camera's image pickup device N through the imaging lens L include those proceeding in parallel with the optical axis La before passing through the imaging lens L (solid line R11 to solid line R12), those proceeding in parallel with the optical axis La after passing through the imaging lens L (solid line R13 to solid line R14), etc.

Such rays of light propagating from the tip end part Ob1t of the first object Ob1 through the imaging lens L are focused by the imaging lens L and converged on a point (tip end part Imt) on the camera's image pickup device M arranged at a position a distance Q rightward from the center Lc of the imaging lens L. Rays of light propagating from other parts of the first object Ob1 also reach the image pickup device M through similar paths, by which the whole of the first object Ob1 is imaged on the image pickup device M as the image Im.

Let us consider here the change of the object of imaging from the first object Ob1 indicated by the solid line arrow to a second object Ob2 indicated by the broken line arrow. The length of the second object Ob2 (the length of the broken line arrow) is assumed to be equal to that of the first object Ob1 (the length of the solid line arrow) for the sake of simplicity.

The second object Ob2 is placed at a position a distance P2 leftward from the center Lc of the imaging lens L. Compared with the first object Ob1, the second object Ob2 is situated ΔP (=P2−P1) farther from the imaging lens L. Here, a glass plate G as a transparent member having two surfaces in parallel with each other (corresponding to the glass plates 916 and 101G) is arranged between the imaging lens L and the second object Ob2 as a method for forming the image of the second object Ob2 on the image pickup device M without changing the distance between the center Lc of the imaging lens L and the image pickup device M from that (distance Q) at the time of the imaging of the first object Ob1.

Since the refractive index n of glass is approximately 1.5 (relative to the refractive index n0 of air normalized to 1), light propagating from the tip end part Ob2t of the second object Qb2 proceeds along the following paths:

First, light (indicated by the broken line R21) proceeding in parallel with the optical axis La before passing through the imaging lens L will be considered below. After the light (broken line R21) reaches the position of the tip end part Ob1t of the first object Ob1 existed before the change of the object, the light is incident vertically upon the two surfaces Gs1 and Gs2 of the glass plate G. Therefore, the light propagates straight without change and thereafter proceeds along the same path as that in the case of the first object Ob1 (solid line R11 to solid line R12).

Next, light proceeding in parallel with the optical axis La after passing through the imaging lens L will be considered below. The light propagates so that its path after emerging from the surface Gs2 of the glass plate G coincides with the path in the case of the first object Ob1 (solid line R13), and thus the light proceeds along the path of broken line R230 to broken line R231 and the path of solid line R13 to solid line R14. Here, the broken line R230 represents the path between the tip end part Ob2t of the second object Ob2 and the surface Gs1 of the glass plate G, and the broken line R231 represents the path inside the glass plate G between the surfaces Gs1 and Gs2.

The light propagating like broken line R230 to broken line R231 is refracted at the surface Gs1 of the glass plate G, while the light propagating like broken line R231 to solid line R13 is refracted at the surface Gs2 of the glass plate G. As above, rays of light propagating from the tip end part Ob2t of the second object Ob2 are focused (along the solid lines R12, R14, etc.) and converged on a point (tip end part Imt) on the image pickup device H in the same way as the aforementioned rays of light propagating from the tip end part Ob1t of the first object Ob1. Rays of light propagating from other parts of the second object Ob2 also reach the image pickup device M through similar paths, by which the whole of the second object Ob2 is imaged on the image pickup device M as the image Im. The result of the imaging of the second object Ob2 is identical with that of the first object Ob1.

Here, the relationship between the difference ΔP in the positions of the second object Ob2 and the first object Ob1 and the thickness Gt of the glass plate G will be considered. Since the refractive index n of glass is approximately 1.5 (relative to the refractive index n0 of air normalized to 1) as mentioned above, the following expression (1) holds:

$$\Delta P = Gt/n0 - Gt/n \quad (1)$$
$$= Gt/1 - Gt/1.5$$
$$= Gt/3$$

For example, by using a glass plate 6 mm in thickness, the second object Ob2 placed at a position P2 2 mm farther from the lens L than the position P1 of the first object Ob1 can be imaged on the same image pickup device M (used for the first object Ob1) without the need of adjusting the camera (changing the distance Q or moving the entire camera along the optical axis La).

Figure 2:
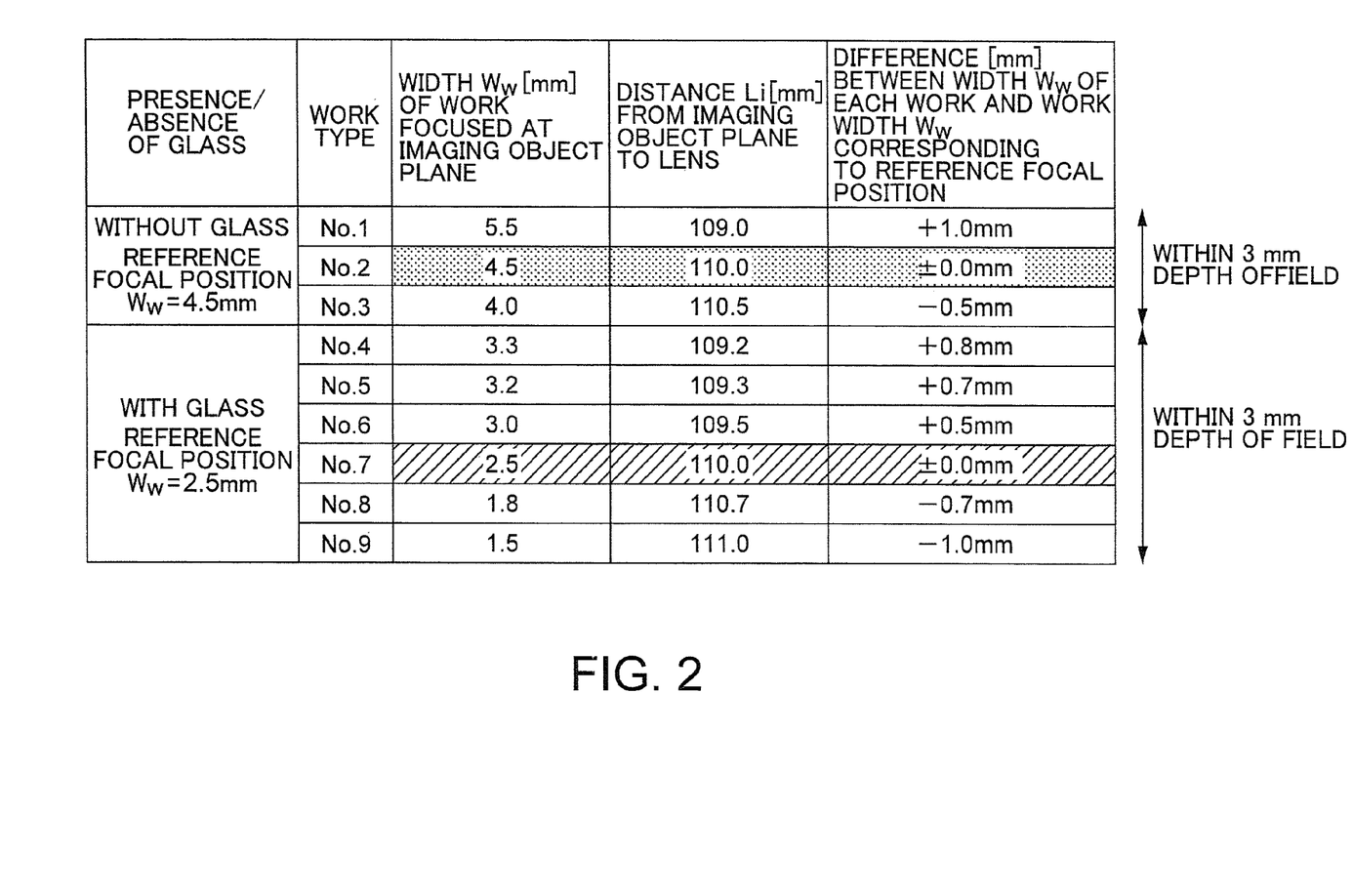
FIG. 2 is a table showing an example of the operation of an inner surface camera unit of the work visual inspection device in accordance with the present invention.
Figure 3:
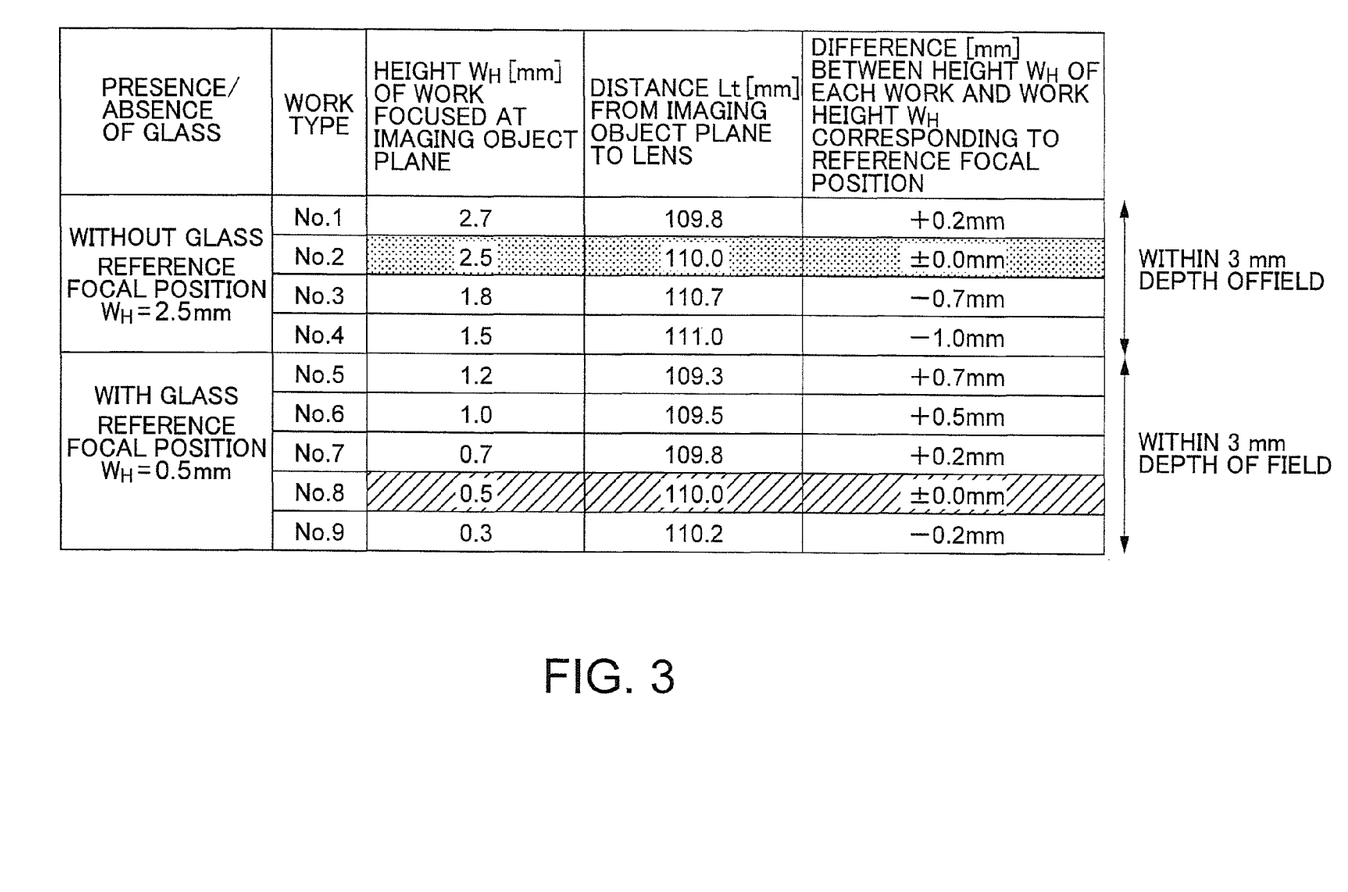
FIG. 3 is a table showing an example of the operation of an upper surface camera unit of the work visual inspection device in accordance with the present invention.

FIGS. 2 and 3 are tables for explaining the focusing (focal adjustment) of the camera 91 of the inner surface camera unit 9 and the camera 101 of the upper surface camera unit 10 in the work visual inspection device 30 according to the basic principle shown in FIG. 1.

In FIGS. 2 and 3, the "imaging lens", the "glass plate" and the "distance to the center of the imaging lens" are expressed simply as "LENS", "GLASS" and "DISTANCE TO LENS", respectively, and thus such expressions will also be used in the following explanation of FIGS. 2 and 3. FIG. 2 shows a case where the image capturing is performed on works of various types No. 1-No. 9 (differing in the length WW of each side in the width direction shown in FIG. 8A) by applying the basic principle of FIG. 1 to the inner surface camera unit 9 shown in FIGS. 7 and 9.

With the lens used in this example, the distance from the imaging object plane (plane as the object of imaging, placed at the reference focal position (most focused position) of the lens) to the lens is 110.0 mm. The depth of field is 3 mm.

The contents of the table of FIG. 2 will be explained below. The leftmost column in FIG. 2 indicates the presence/absence of the glass. Specifically, "WITHOUT GLASS" indicates image capturing performed without arranging the glass plate G in the configuration of FIG. 1, while "WITH GLASS" indicates image capturing performed by arranging the glass plate G. The "REFERENCE FOCAL POSITION" in the column means the most focused position of the employed lens as mentioned above. In the case of the employed lens, the work having the width WW=4.5 mm corresponds to the reference focal position as described in the column "WITHOUT GLASS". The thickness of the glass in the case "WITH GLASS" is 6 mm, and thus $\Delta P$ equals 2 mm according to the above expression (1). Thus, the reference focal position in the case "WITH GLASS" is 2.5 mm (WW=2.5 mm), which is 2 mm shorter than WW=4.5 mm of the case "WITHOUT GLASS".

In this example, the second object Ob2 is situated farther and leftward from the imaging lens L than the first object Ob1 in the basic principle of FIG. 1. In FIG. 9, the distance Li2 between the center 91Lc of the imaging lens 91L and the inner surface W2i of the work W2 in the inner surface camera unit 9 is greater than the distance Li1 between the center 91Lc of the imaging lens 91L and the inner surface W1i of the work W1. The reason why the value of WW in the case "WITH GLASS" is smaller than the value in the case "WITHOUT GLASS" in the leftmost column in FIG. 2 corresponds to the positional relationship in the basic principle of FIG. 1 and the above magnitude relationship (distance relationship) shown in FIG. 9.

The second column from the left in FIG. 2 indicates the work types discriminated by the value of WW. Each work, (work type) is assigned a number from No. 1 to No. 9.

The third column from the left in FIG. 2 indicates the width WW of the work that is focused at the imaging object plane. The value of the width WW is shown in regard to each work (each work type) described in the work type column. To allow the lens to focus on works of all work types, the works No. 1-No. 3 are assigned "WITHOUT GLASS" and the works No. 4-No. 9 are assigned "WITH GLASS".

In this example, the reference focal position in the case where the work No. 2 is shot "WITHOUT GLASS" is WW =4.5 mm, and thus the row of the work No. 2 is emphasized with hatching to indicate the fact. Similarly, the reference focal position in the case where the work No. 7 is shot "WITH GLASS" is WW=2.5 mm, and thus the row of the work No. 7 is also emphasized with hatching to indicate the fact. The lens can focus on any work within ±1.5 mm of the reference focal position since the depth of field of the employed lens is 3 mm. Thus, in the state in which the lens "WITHOUT GLASS" is focused on the reference focal position (WW=4.5 mm), the lens can focus on any work as long as its width WW is within the range of 4.5 mm±1.5 mm.

The widths WW of the works No. 1 and No. 3 are 5.5 mm and 4.0 mm, respectively. Since these WW values are within the range of 4.5 mm±1.5 mm, the works No. 1 and No. 3 can he focused on by the lens "WITHOUT GLASS" as well as the work No. 2. Similarly, in the state in which the lens "WITH GLASS" is focused on the reference focal position (WW=2.5 mm), the lens can focus on any work as long as its width WW is within the range of 2.5 mm±1.5 mm. The widths WW of the works No. 4-No. 6 are 3.3 mm, 3.2 mm and 3.0 mm, respectively. The widths WW of the works No. 8 and No. 9 are 1.8 mm and 1.5 mm, respectively. Since these WW values are all within the range of 2.5 mm±1.5 mm, the works No. 4-No. 6 and the works No. 8 and No. 9 can be focused on by the lens "WITH GLASS" as well as the work No. 7.

The fourth column from the left in FIG. 2 indicates the distance Li from the imaging object plane to the lens. The distance Li corresponds to the distance Li1/Li2 between the center 91Lc of the imaging lens 91L and the inner surface W1i/W2i of the work W1/W2 in the inner surface camera unit 9 shown in FIG. 9. The distances U at the reference focal position (works No. 2 and No. 7) in the cases "WITHOUT GLASS" and "WITH GLASS" are both 110.0 mm as mentioned above. These rows in the distance column are also emphasized with the hatching representing the reference focal position. In the case of the work No. 1, the WW value (width) is 1.0 mm greater than that of the work No. 2 corresponding to the reference focal position, and thus the Li value (distance) conversely becomes 1.0 mm smaller than that of the work No. 2. This corresponds to the fact that the distance Li1 between the center 91Lc of the imaging lens 91L and the inner surface W1i of the work W1 (having a greater width WW) is shorter than the distance Li2. between the center 91Lc of the imaging lens 91L and the inner surface. W2i of the work W2 (having a less width WW) in the inner surface camera unit 9 shown in FIG. 9.

In the case of the work No. 3, the WW value (width) is 0.5 mm less than that of the work No. 2 corresponding to the reference focal position, and thus the Li value (distance) conversely becomes 0.5 mm greater than that of the work No. 2 for the same reason. When the work No. 7 is used for the reference focal position, the distances Li of the works No. 4-No. 6 (having widths WW greater than that of the work No. 7) become less than that of the work No. 7 by the differences in the width WW, while the distances Li of the works No. 8 and No. 9 (having widths WW less than that of the work No. 7) become greater than that of the work No. 7 by the differences in the width WW.

The rightmost column in FIG. 2 indicates the difference between the width WW of each work and the width WW of the work, corresponding to the reference focal position. As mentioned above, the work No. 2 corresponds to the reference focal position in the cases "WITHOUT GLASS" and the work No. 7 corresponds to the reference focal position in the cases "WITH GLASS". The rows of the works No. 2 and No. 7 are hatched in order to indicate the fact. The value (difference) in each hatched row is ±0.0 mm.

The width difference from the work No. 2 is described in each of the rows of the works No. 1 and No. 3, while the width difference from the work No. 7 is described in each of the rows of the works No. 4-No. 6, No. 8 and No. 9. These differences are all within ±1.5 mm (of the reference focal position), indicating that all the works are within the range (3 mm) of the depth of field.

If the image capturing is carried out by exclusively using the reference focal position WW=4.5 mm of the cases "WITHOUT GLASS" (without setting the reference focal position for the cases "WITH GLASS"), the works No. 7-No. 9 deviate from the WW range of 4.5 mm±1.5 mm and thus the image capturing becomes impossible. Therefore, it is clear in this example that the range of works that can be shot in focus without the need of adjusting the camera is extended by the present invention.

FIG. 3 shows a case where the image capturing is performed on the works of the types No. 1-No. 9 (differing in the length WH of each side in the height direction shown in FIG. 8A) by applying the basic principle of FIG. 1 to the upper surface camera unit 10 shown in FIGS. 7 and 10. With the lens used in this example, the distance from the imaging object plane (placed at the reference focal position (most focused position) of the lens) to the lens is 110.0 mm. The depth of field is 3 mm.

In FIG. 3, the height WH of each work is shown and the distance from the imaging object plane to the lens is represented as Lt. The distance Lt corresponds to the distance Lt1/Lt2 between the center 101Lc of the imaging lens 101L and the upper surface W1t/W2t of the work W1/W2 in the upper surface camera unit 10 shown in FIG. 10.

The other parts of FIG. 3 are substantially the same as those of FIG. 2. In FIG. 3, WH equals 2.5 mm at the reference focal position for "WITHOUT GLASS". This corresponds to the work No. 2, and thus the row of the work No. 2 is emphasized with hatching. The works No. 1-4 are all shot "WITHOUT GLASS" and their WH differences from the work No. 2 corresponding to the reference focal position are within the 3 mm range of the depth of field. The thickness of the glass is 6 mm. In the cases "WITH GLASS", WH at the reference focal position is 0.5 mm (2 mm shorter compared to the cases "WITHOUT GLASS"), This corresponds to the work No. 8, and thus the row of the work No. 8 is emphasized with hatching.

The works No. 5-9 are all shot "WITH GLASS" and their WH differences from the work No. 8 corresponding to the reference focal position are within the 3 mm range of the depth of field. If the image capturing is carried out by exclusively using the reference focal position WW=2.5 mm of the cases "WITHOUT GLASS" (without setting the reference focal position for the cases "WITH GLASS"), the works No. 7-No. 9 deviate from the WW range of 2.5 mm±1.5 mm and thus the image capturing becomes impossible. Therefore, it is clear also in this example (like in the example of FIG. 2) that the range of works that can be shot in focus without the need of adjusting the camera is extended by the present invention.

The image capturing of the works W1 and W2 by the upper surface camera unit 10 is carried out as described above.

Subsequently, each work W1/W2 after undergoing the image capturing by the upper surface camera unit 10 is conveyed as shown in FIG. 10 to the position <6> corresponding to the lower surface camera unit 11 via the positions <4> and <5> by the rotation of the conveyance table 2 in the direction of the arrow X. In this case, the lower surfaces W1b and W2b to be shot are situated substantially on the same plane. In the lower surface camera unit 11, a camera 111 is arranged under the conveyance table 2. The camera 111, having a body tube 111C storing an imaging lens 111L, captures an image of the lower surface W1b/W2b of the work W1/W2 with a photoreceptor device 111A when the approximate center of the lower surface W1b/W2b coincides with the optical axis 111La (position <6>). At this point, the distance Lb between the center 111Lc of the imaging lens 111L and the lower surface W1b/W2b to be shot is substantially equal between the works W1 and W2.

In other words, at the position <6> of the lower surface camera unit 11, both the lower surfaces W1b and W2b are situated at the same focal position of the imaging lens 111L. Therefore, no problem occurs in the image capturing in the lower surface camera unit 11 even when the inspection object work is changed from a large work W1 to a small work W2.

Figure 11:
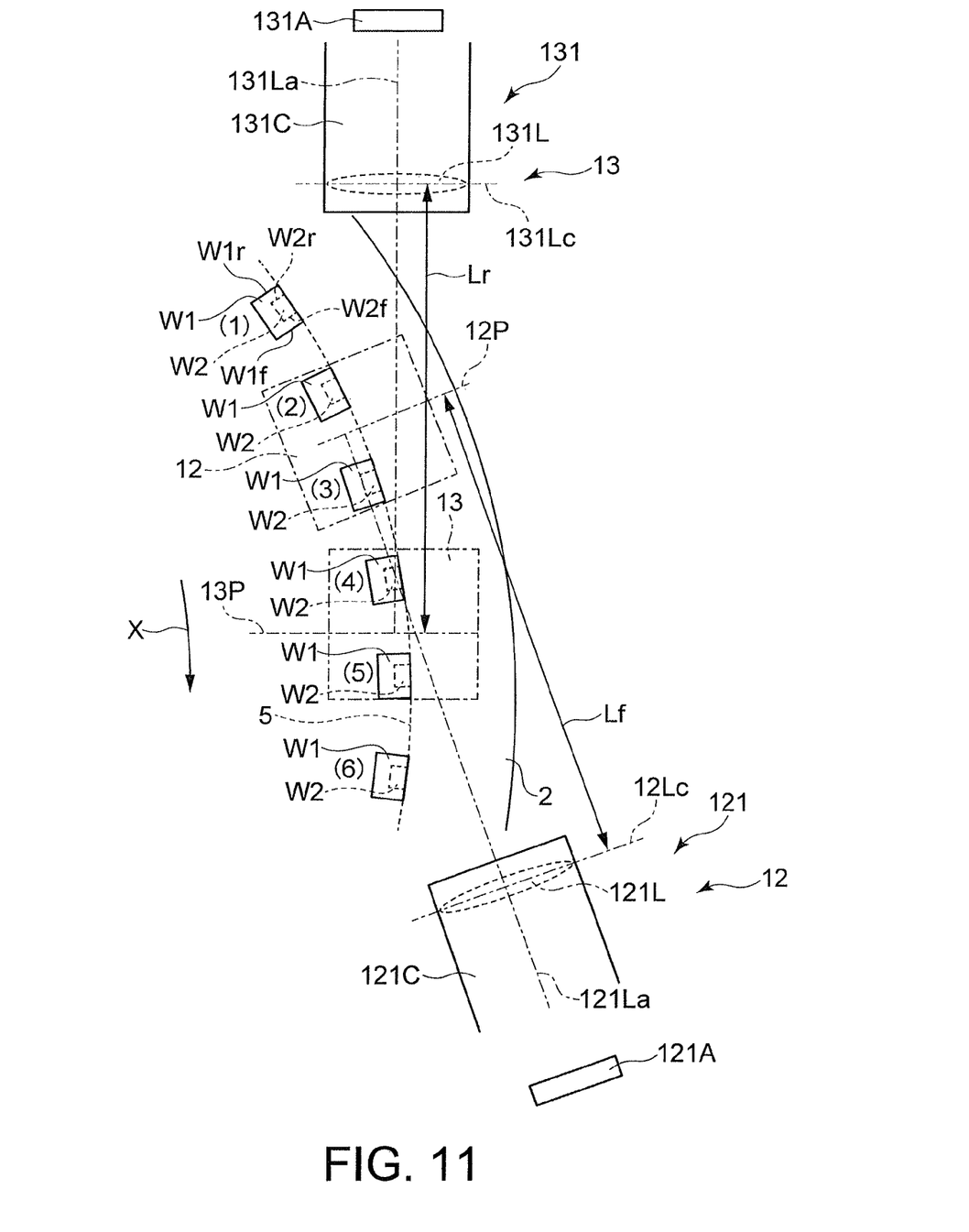
FIG. 11 is an enlarged view showing an area S3 in FIG. 7.

FIG. 11 is an enlarged view of the area S3 in FIG. 7 in the vicinity of the front surface camera unit 12 and the rear surface camera unit 13. In FIG. 11, the work W1 before the work type change is indicated by solid lines and the work W2 after the work type change is indicated by broken lines in the same ways as FIG. 9. Similarly to FIG. 9, positions of the work W1/W2 along the time line are indicated by the numbers (1)-(6) along the conveyance path of the work W1/W2. As mentioned above, each work W1/W2 has been set on the top of the conveyance table 2 so that its side surface W1s/W2s faces the outside of the conveyance table 2 and is situated on the tangential line of the work conveyance arc 5.

Each work W1/W2 is conveyed from the position (1) to the front surface camera unit 12 by the rotation of the conveyance table 2 in the direction of the arrow X and reaches the position (3) via the position (2). On this path, the front surface W1f/W2f of the work W1/W2 (indicated at the position (1)) crosses the focal position 12P situated between the positions (2) and (3).

In the front surface camera unit 12, a camera 121 is arranged at a position outside the conveyance table 2 and in the rotational direction of the conveyance table 2 from the focal position 12P. The camera 121, having a body tube 121C storing an imaging lens 121L, captures an image of the front surface W1f/W2f of the work W1/W2 with a photoreceptor device 121A when the front surface W1f/W2f crosses the focal position 12P.

At this point, the distance lf between the center 121Lc of the imaging lens 121L and the front surface W1f/W2f to be shot is substantially equal between the works W1 and W2. In other words, in the front surface camera unit 12, both the front surfaces W1f and W2f are shot when they are situated at the same focal position of the imaging lens 121L Therefore, no problem occurs in the image capturing in the front surface camera unit 12 even when the inspection object work is changed from a large work W1 to a small work W2.

Subsequently, the work W1/W2 is conveyed from the position (3) to the rear surface camera unit 13 by the rotation of the conveyance table 2 in the direction of the arrow X and reaches the position (5) via the position (4). On this path, the rear surface W1r/W2r of the work W1/W2 (indicated at the position (1)) crosses the focal position 13P situated between the positions (4) and (5).

In the rear surface camera unit 13, a camera 131 is arranged at a position outside the conveyance table 2 and in a direction reverse to the rotational direction of the conveyance table 2 from the focal position 13R The camera 131, having a body tube 131C storing an imaging lens 131L, captures an image of the rear surface W1r/W2r of the work W1/W2 with a photoreceptor device 131A when the rear surface W1r/W2r crosses the focal position 13P.

At this point, the distance Lr between the center 131Lc of the imaging lens 131L and the rear surface W1r/W2r to be shot is substantially equal between the works W1 and W2. In other words, in the rear surface camera unit 13, both the rear surfaces W1r and W2r are shot when they are situated at the same focal position of the imaging lens 131L. Therefore, no problem occurs in the image capturing in the rear surface camera unit 13 even when the inspection object work is changed from a large work Wi to a small work W2.

As described above, in the work visual inspection device 30 according to this embodiment, when the inspection object work is changed from a large work. W1 to a small work W2, the focal adjustment can be made for the cameras 91 and 101 of the inner surface camera unit 9 and the upper surface camera unit 10 (for shooting two of the six surfaces) in an easy and simple manner, by attaching the second body tubes 91Ca and 101Ca to the first body tubes 91C and 101C. Therefore, the visual inspection of works can be performed efficiently, with no heavy load on the operator for the focal adjustment of the cameras 91 and 101.

What is claimed is:

1. A work visual inspection device comprising:
a work conveyance module which holds and conveys works including a first work and a second work of a shape different from that of the first work, the side surfaces of the first and second works facing the outside of the work conveyance module being situated on a same plane or being situated on a tangential line of a work conveyance arc; and
a work imaging module which captures images of the works conveyed by the work conveyance module, wherein the work imaging module includes:
a first front body tube including an imaging lens for capturing an image of a front surface of the work and sending the image to a light receiving element, and
a second front body tube attached to an end of the first front body tube, the end of the first front body tube being the one in the vicinity of the imaging lens, and including a transparent member for focal adjustment having two surfaces in parallel with each other, wherein the second front body tube is attached to the first front body tube by screwing the second front body tube into the first front body tube without changing a focal length of the imaging lens or a length between the imaging lens and the light receiving element when changing a work to be inspected from the first work to the second work;
a first side body tube including an imaging lens for capturing an image of a side surface of the work, and
a second side body tube attached to an end of the first side body tube, the end of the first side body tube being the one in the vicinity of the imaging lens, and including a transparent member for focal adjustment having two surfaces in parallel with each other, wherein the second side body tube is attached to the first side body tube by screwing the second side body tube into the first side body tube when changing a work to be inspected from the first work to the second work;
wherein a difference between a distance Li2 between a center of the imaging lens and an inner surface of the second work to be captured in an image after a work type change and a distance Li1 between the center of the imaging lens and the inner surface of the first work captured in an image before the work type change, namely, a difference ΔLi is within a range of a depth of field of the imaging lens, wherein the depth of field is a focal range of the imaging lens for capturing an image in a focused state even when the first and second works are positioned slightly closer to or farther from a focal position of the imaging lens.

2. The work visual inspection device according to claim 1, wherein the transparent member is formed of a glass plate.

3. A work visual inspection method comprising:
a work conveyance step of holding and conveying works with a work conveyance module; and
a work imaging step of capturing an image of the conveyed work with a work imaging module, wherein the work imaging step includes:
a first front work imaging step of allowing the work imaging module to capture an image of a front surface of a first work and sending the image to a light receiving element, with the work imaging module including a first front body tube including an imaging lens, and
a second front work imaging step of allowing the work imaging module to capture an image of a front surface of a second work of a shape different from the first work, the side surfaces of the first and second works facing the outside of the work conveyance module being situated on a same plane or being situated on a tangential line of a work conveyance arc, with the work imaging module including the first front body tube and a second front body tube, the second front body tube being attached to an end of the first front body tube, the end of the first front body tube being the one in the vicinity of the imaging lens, and including a transparent member for focal adjustment having two surfaces in parallel with each other, wherein the second front body tube is attached to the first front body tube by screwing the second front body tube into the first front body tube without changing a focal length of the imaging lens or a length between the imaging lens and the light receiving element when changing a work to be inspected from the first work to the second work;
a first side work imaging step of allowing the work imaging module to capture an image of a side surface of a first work, with the work imaging module including a first side body tube including an imaging lens, and
a second side work imaging step of allowing the work imaging module to capture an image of a side surface of a second work of a shape different from the first work, the side surfaces of the first and second works facing the outside of the work conveyance module being situated on a same plane or being situated on a tangential line of a work conveyance arc, with the work imaging module including the first side body tube and a second side body tube, the second side body tube being attached to an end of the first side body tube, the end of the first side body tube being the one in the vicinity of the imaging lens, and including a transparent member for focal adjustment having two surfaces in parallel with each other, wherein the second body tube is attached to the first side body tube by screwing the second side body tube into the first side body tube when changing a work to be inspected from the first work to the second work;
wherein a difference between a distance Li2 between a center of the imaging lens and an inner surface of the second work to be captured in an image after a work type change and a distance Li1 between the center of the imaging lens and an inner surface of the first work captured in an image before the work type change, namely, a difference ΔLi is within a range of a depth of field of the imaging lens, wherein the depth of field is a focal range of the imaging lens for capturing an image in a focused state even when the first and second works are positioned slightly closer to or farther from a focal position of the imaging lens.

4. The work visual inspection method according to claim 3, wherein the transparent member is formed of a glass plate.

* * * * *